US00PP21022P2

(12) United States Plant Patent
Blom

(10) Patent No.: US PP21,022 P2
(45) Date of Patent: May 25, 2010

(54) ***ECHINACEA* PLANT NAMED 'HOT PAPAYA'**
(50) Latin Name: *Echinacea hybrida*
Varietal Denomination: Hot Papaya

(76) Inventor: Arie Blom, Waterbieslaan 110, 3452 AR Vleuten (NL)

( * ) Notice: Subject to any disclaimer, the term of this patent is extended or adjusted under 35 U.S.C. 154(b) by 0 days.

(21) Appl. No.: 12/319,413

(22) Filed: Jan. 7, 2009

(51) Int. Cl.
*A01H 5/00* (2006.01)

(52) U.S. Cl. ..... Plt./428

(58) Field of Classification Search ..... Plt./428
See application file for complete search history.

*Primary Examiner*—June Hwu
(74) *Attorney, Agent, or Firm*—C. A. Whealy

(57) ABSTRACT

A new and distinct cultivar of *Echinacea* plant named 'Hot Papaya', characterized by it upright plant habit; moderately vigorous growth habit; strong and thick flowering stems; freely basal branching habit; and large anemone-type inflorescences with orange red-colored ray and disc florets.

2 Drawing Sheets

Botanical designation: *Echinacea hybrida.*
Cultivar denomination: 'HOT PAPAYA'.

BACKGROUND OF THE INVENTION

The present invention relates to a new and distinct cultivar of *Echinacea* plant, botanically known as *Echinacea hybrida*, and hereinafter referred to by the name 'Hot Papaya'.

The new *Echinacea* plant originated from an open-pollination in 2005 in Vleuten, The Netherlands of a proprietary selection of *Echinacea hybrida* identified as code number Ec 512-17, not patented, as the female, or seed, parent with an unknown selection of *Echinacea hybrida* as the male, or pollen, parent. The new *Echinacea* was discovered and selected by the Inventor as a single flowering plant from within the progeny of the stated open-pollination grown in an outdoor nursery environment in Zuidwolde, The Netherlands in July, 2007.

Asexual reproduction of the new *Echinacea* plant by micropropagation a controlled greenhouse environment in Enkhuizen, The Netherlands since November, 2007, has shown that the unique features of this new *Echinacea* plant are stable and reproduced true to type in successive generations.

SUMMARY OF THE INVENTION

Plants of the new *Echinacea* have been observed under all possible environmental conditions. The phenotype may vary somewhat with variations in environment such as temperature and light intensity, without, however, any variance in genotype.

The following traits have been repeatedly observed and are determined to be the unique characteristics of 'Hot Papaya'. These characteristics in combination distinguish 'Hot Papaya' as a new and distinct cultivar of *Echinacea:*

1. Upright plant habit.
2. Moderately vigorous growth habit.
3. Strong and thick flowering stems.
4. Freely basal branching habit.
5. Large anemone-type inflorescences with orange red-colored ray and disc florets.

Plants of the new *Echinacea* plant can be compared to plants of the female parent selection. Plants of the new

*Echinacea* plant differ from plants of the female parent selection in the following characteristics:

1. Plants of the new *Echinacea* are more freely branching than plants of the female parent selection.
2. Plants of the new *Echinacea* have broader leaves than plants of the female parent selection.
3. Plants of the new *Echinacea* have larger inflorescences than plants of the female parent selection.

Plants of the new *Echinacea* can be compared to plants of *Echinacea hybrida* 'Razzmatazz' , disclosed in U.S. Plant Pat. No. 13,894. In side-by-side comparisons, plants of the new *Echinacea* differed from plants of 'Razzmatazz' in the following characteristics:

1. Plants of the new *Echinacea* were more freely branching than plants of 'Razzmatazz'.
2. Plants of the new *Echinacea* had longer leaves than plants of 'Razzmatazz'.
3. Plants of the new *Echinacea* flowered earlier than plants of 'Razzmatazz'.
4. Plants of the new *Echinacea* and 'Razzmatazz' differed in floret coloration as plants of 'Razzmatazz' had dark pink-colored ray florets and red purple-colored disc florets.

BRIEF DESCRIPTION OF THE PHOTOGRAPHS

The accompanying photographs illustrate the overall appearance of the new *Echinacea*. The photographs show the colors as true as it is reasonably possible to obtain in colored reproductions of this type. Colors in the photographs may differ slightly from the color values cited in the detailed botanical description which accurately describe the colors of the new *Echinacea.*

The photograph on the first sheet comprises a side perspective view of typical flowering stems of 'Hot Papaya'.

The photograph at the top of the second sheet is a close-up view of a typical inflorescence of 'Hot Papaya'.

The photograph at the bottom of the second sheet is a close-up view of the upper surface of a typical leaf of 'Hot Papaya'.

DETAILED BOTANICAL DESCRIPTION

The aforementioned photographs and following observations and measurements describe plants grown in Zuidwolde, The Netherlands during the summer in an outdoor nursery and under conditions and practices which approximate those generally used in commercial *Echinacea* production. During the production of the plants, day temperatures ranged from 12° C. to 30° C. and night temperatures ranged from 3° C. to 14° C. Measurements and numerical values represent averages for typical flowering plants. Plants had been growing for six months when the photographs and description were taken. In the following description, color references are made to The Royal Horticultural Society Colour Chart, 2001 Edition, except where general terms of ordinary dictionary significance are used.

Botanical classification: *Echinacea hybrida* 'Hot Papaya'.

Parentage:

*Female parent.*—Proprietary selection of *Echinacea hybrida* identified as code number Ec 512-17, not patented.

*Male parent.*—Unknown selection of *Echinacea hybrida,* not patented.

Propagation:

*Type.*—By micropropagation.

*Time to initiate roots.*—About one week at 25° C.

*Time to produce a rooted young plant.*—About five weeks at 21° C.

*Root description.*—Fine, fibrous; pale creamy white in color.

*Rooting habit.*—Freely branching; moderately dense.

Plant description:

*Plant form/growth habit.*—Upright and columnar plant habit; freely basal branching; moderately vigorous growth habit.

*Plant height.*—About 70.6 cm.

*Plant diameter or spread.*—About 30 cm.

*Basal branches.*—Length: About 30.9 cm. Diameter: About 8 mm. Internode length: About 5.5 cm. Aspect: Upright. Strength: Strong. Texture: Smooth, glabrous. Color: Close to 144A tinged with close to N186C.

Foliage description:

*Arrangement.*—Alternate, simple.

*Length.*—About 18.1 cm.

*Width.*—About 7 cm.

*Shape.*—Narrowly ovate to lanceolate.

*Apex.*—Narrowly acute.

*Base.*—Attenuate to narrowly cuneate.

*Margin.*—Entire, slightly sinuate.

*Texture, upper and lower surfaces.*—Pubescent; rough.

*Venation pattern.*—Pinnate.

*Color.*—Developing leaves, upper surface: Close to 137B. Developing leaves, lower surface: Close to 137C. Fully expanded leaves, upper surface: Close to 147A; venation, close to 147C to 147D. Fully expanded leaves, lower surface: Close to 147B; venation, close to 147D.

*Petioles.*—Length: About 3.1 cm. Diameter: About 4 mm. Texture, upper surface: Smooth, glabrous. Texture, lower surface: Pubescent; slightly rough. Color, upper and lower surfaces: Close to 146D.

Inflorescence description:

*Appearance.*—Rotate anemone-type inflorescence form with ray and disc florets arranged acropetally on a capitulum; inflorescences positioned above the foliage on strong and thick peduncles facing upright.

*Quantity of inflorescences per plant.*—About eight inflorescences develop per flowering stem.

*Fragrance.*—None detected.

*Time to flower.*—Plants flower continuously from early July to late September in The Netherlands.

*Inflorescence longevity.*—Inflorescences maintain good substance for about three weeks on the plant; inflorescences not persistent.

*Inflorescence bud.*—Height: About 1.8 cm. Diameter: About 2.7 cm. Shape: Flattened globular. Color: Between 143A and 146A.

*Inflorescence size.*—Diameter: About 9.3 cm. Depth (height): About 6 cm. Disc diameter: About 3.8 cm. Receptacle height: About 2.4 mm. Receptacle diameter: About 1.3 cm. Receptacle color: Close to 155B.

*Ray florets.*—Length: About 6.1 cm. Width: About 1.1 cm. Shape: Narrowly oblanceolate. Apex: Emarginate to praemorse. Base: Cuneate. Margin: Entire. Texture, upper and lower surfaces: Smooth, glabrous; longitudinally ridged. Number of ray florets per inflorescence: About 23 arranged in a single whorl. Aspect: Horizontal to reflexing. Color: When opening, upper surface: Close to N34A to N34B. When opening, lower surface: Close to 53A. Fully opened, upper surface: Between 34A and N34A; towards the base, close to between N34A and 42A. Fully opened, lower surface: Close to 184B to 184C; stripes, close to 153C to 153D.

*Disc florets.*—Length: About 2.6 cm. Diameter: About 6 mm. Shape: Tubular, enlarged; apices praemorse. Number of disc florets per inflorescence: About 400. Texture, upper and lower surfaces: Smooth, glabrous. Color: Immature, inner surface: Close to N34A to N34B. Immature, outer surface: Close to 53A. Mature, inner surface: Between 34A and N34A; towards the base, close to between N34A and 42A. Mature, outer surface: Close to 184B to 184C.

*Receptacle spines.*—Quantity: One per disc floret. Shape: Acicular. Apex: Acute. Base: Attenuate. Texture: Smooth, glabrous. Color: Apex: Close to 46A. Mid-section: Close to 144A. Base: Close to 145A to 145B.

*Involucral bracts.*—Quantity per inflorescence: About 50 in about three whorls. Length: About 1.1 cm. Width: About 4 mm. Shape: Narrowly ovate. Apex: Acute. Base: Cuneate. Margin: Entire. Texture, upper surface: Smooth, glabrous. Texture, lower surface: Sparsely pubescent. Color, upper surface: Close to 137A; towards the base, close to 144B. Color, lower surface: Close to 138A.

*Peduncles.*—Length, terminal peduncle: About 25.8 cm. Length, fourth peduncle: About 27.8 cm. Diameter: About 4 mm. Strength: Strong. Aspect: Upright to about 30° from vertical. Texture: Sparsely pubescent. Color: Close to 145A speckled with close to 177B.

*Reproductive organs.*—Androecium (present on ray and disc florets): Quantity per floret: About two. Filament length: About 3 mm. Filament color: Close to 164C to 164D. Anther shape: Oblong. Anther length: About 2 mm. Anther color: Close to N199B. Pollen amount: Moderate. Pollen color: Close to 13C to 13D. Gynoecium (present only on disc florets): Quantity per floret: One. Pistil length: About 7 mm. Stigma shape: Elongate. Stigma color: Close to 187A. Style length: About 6 mm. Style color: Close to 47D. Ovary color: Close to 157A to 157B.

*Fruits/seeds.*—Fruit and seed development have not been observed.

Disease/pest resistance: Plants of the new *Echinacea* have not been shown to be resistant to pathogens and pests common to *Echinacea.*

Garden performance: Plants of the new *Echinacea* have exhibited good tolerance to rain and wind, have been observed to tolerate temperatures ranging from about −20° C. to about 45° C.

It is claimed:

1. A new and distinct *Echinacea* plant named 'Hot Papaya' as illustrated and described.

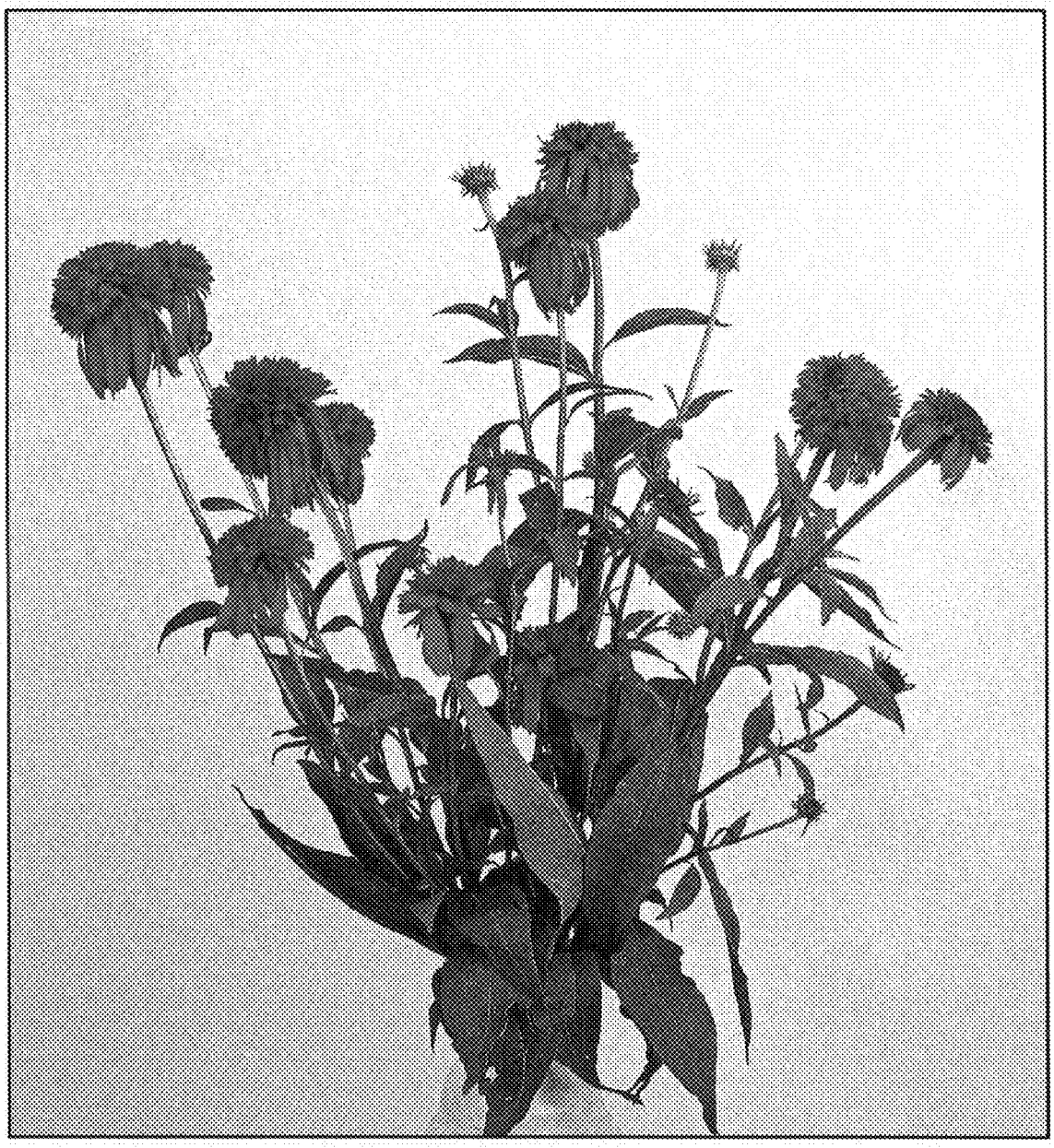

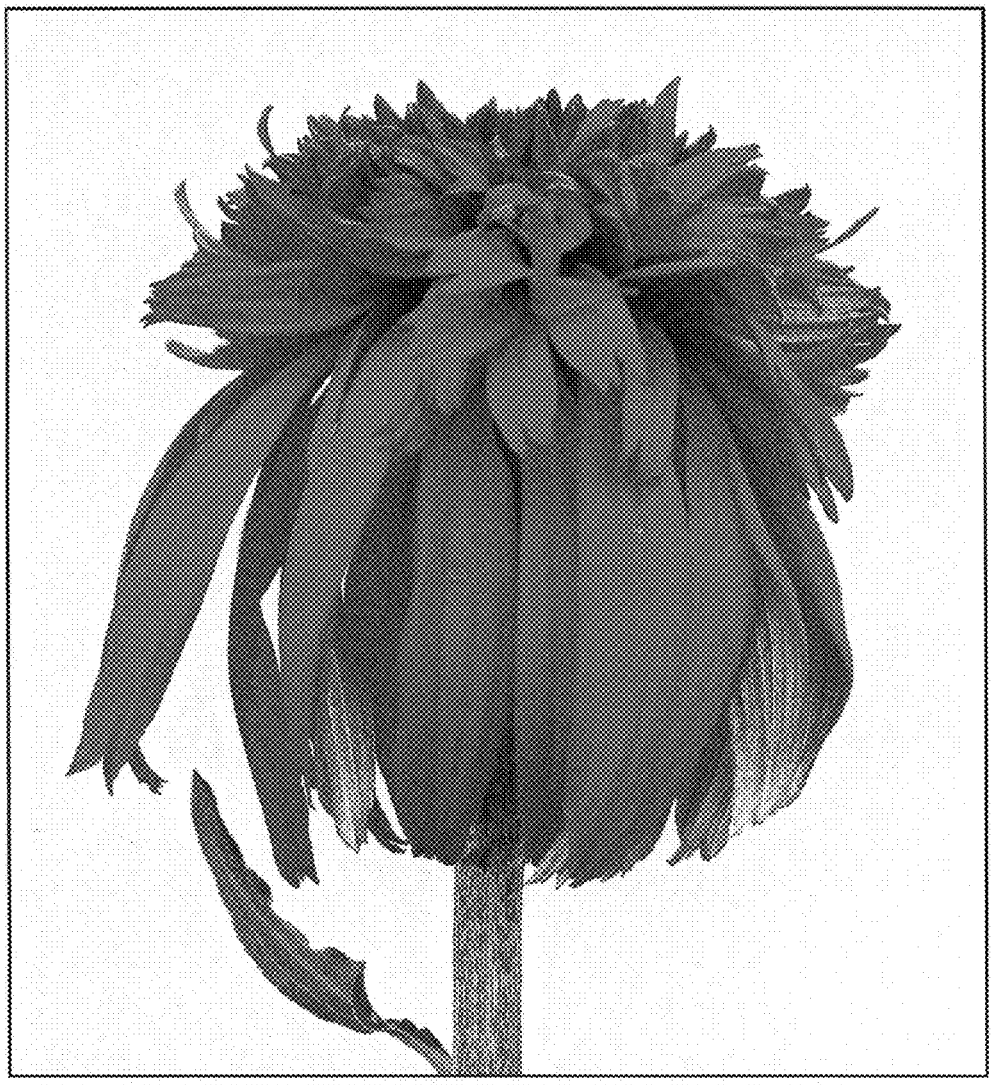
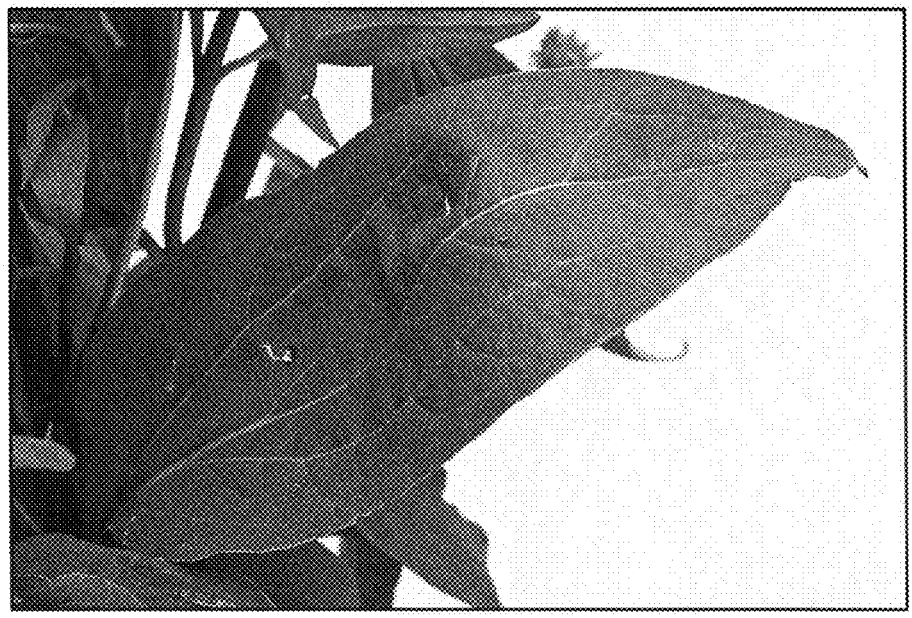

* * * * *